United States Patent [19]

Gayle et al.

[11] Patent Number: 5,576,191
[45] Date of Patent: Nov. 19, 1996

[54] CYTOKINE THAT BINDS ST2

[75] Inventors: Margit Gayle, Woodinville; Jennifer L. Slack, Poulsbo; Hans-Juergen Gruss, Bainbridge Island; John E. Sims, Seattle; Steven K. Dower, Redmond, all of Wash.

[73] Assignee: Immunex Corporation, Seattle, Wash.

[21] Appl. No.: 265,086

[22] Filed: Jun. 17, 1994

[51] Int. Cl.$^6$ .......................... A61K 38/17; C07K 14/47; C07H 21/04

[52] U.S. Cl. .......................... 435/69.1; 536/23.5; 530/350; 530/839; 435/320.1; 435/69.7; 424/192.1; 424/193.1

[58] Field of Search .......................... 530/350, 839; 435/69.1, 69.7, 70.1, 172.1, 172.3, 240.2, 252.3, 320.1; 536/23.5, 24.31, 24.33; 424/192.1, 193.1

[56] References Cited

U.S. PATENT DOCUMENTS

| | | |
|---|---|---|
| 5,312,734 | 5/1994 Uhl et al. | 435/69.1 |
| 5,422,262 | 6/1995 Andersson et al. | 435/240.1 |

OTHER PUBLICATIONS

Klemenz et al., *Proc. Natl. Acad. Sci* USA 86:5708, 1989.
Tominaga, *FEBS LETTERS* 258:301, 1989.
Yanagisawa et al., *FEBS LETTERS* 318:83, 1993.
Tominaga et al., *Biochimica et Biophysica Acta* 1171:215, 1992.
McMahan et al, *EMBO J.* 10:2821, 1991.
Goebel et al., *Virology* 179:247, 1990.
Pasquale et al., *Proc. Natl. Acad. Sci.* USA 87:5812, 1990.
Chou and Hayman, *Proc. Natl. Acad. Sci.* USA 88:4897, 1991.
Werenskiold, *Eur. J. Biochem.* 204:1041, 1992.
Bergers et al., *Embo J.* 13:1176, 1994.
Tominaga et al., *Biochimica et Biophysica Acta* 1090:1, 1991.
Printout of Genbank submission No. L22015 excerpt.
Singer–Kruger et al., *J. Biol. Chem.* 268:14376, 1993.
Ashkenazi et al, *Proc. Natl. Acad. Sci.* USA 88:10535, 1991.
Byrn et al., *Nature* 344:667, 1990.
Rössler et al, "T1, an immunoglobulin superfamily member is expressed in H–*ras*–dependent epithelial tumours of mammary cells", *Oncogene* 8:609–617, 1993.
Werenskiold et al., "Induction of a Mitogen–Responsive Gene after Expression of the Ha–*ras* Oncogene in NIH 3T3 Fibroblasts", *Mol. Cell. Biol.* 9:5207–5214, 1989.
Rössler et al., "Expression of T1, a possible morphogenetic factor of the immunoglobulin superfamily, in osteogenesis", Abstract B–22, Conference on Growth Factors, Development, and Cancer, Mar. 5–11, 1994.
Rössler et al., "T1, an interleukin–1 receptor homologue, is a putative immunomodulator of invasive processes in placenta turmorigenesis", Abstract B–17, Conference on Growth Factors, Development, and Cancer, Mar. 5—11, 1994.
Printout of Genbank submission No. X67317.
Printout of Genbank submission No. U00059 excerpt.

*Primary Examiner*—Marianne P. Allen
*Assistant Examiner*—Lorraine Spector
*Attorney, Agent, or Firm*—Kathryn A. Anderson

[57] ABSTRACT

ST2 ligand polypeptides are provided, along with DNA sequences, expression vectors and transformed host cells useful in producing ST2 ligand polypeptides. The ST2 ligand polypeptide binds to a receptor that is expressed on cell types that include certain Hodgkin's Disease-derived tumor cells.

22 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1303 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( B ) CLONE: huST2-lig ( i x ) FEATURE:
        ( A ) NAME/KEY: CDS
        ( B ) LOCATION: 88..771

( i x ) FEATURE:
        ( A ) NAME/KEY: sig_peptide
        ( B ) LOCATION: 88..156

( i x ) FEATURE:
        ( A ) NAME/KEY: mat_peptide
        ( B ) LOCATION: 157..768

( x i ) SEQUENCE DESCRIPTION: SEQ ID NO:1:

```
CTGCCAATGA  GCTCCGCCGA  GTAGCACCGG  GGCAGGGCTA  GCGCTTAAAG  GAGCCGCGAC      60
```

```
CCCTTTGCAG ACCAGAGGGT GACCCGG ATG ATG GCG GCC GGC GCG GCC CTA                111
                                Met Met Ala Ala Gly Ala Ala Leu
                                -23                 -20

GCC CTG GCC TTG TGG CTA CTA ATG CCA CCA GTG GAG GTG GGA GGG GCG              159
Ala Leu Ala Leu Trp Leu Leu Met Pro Pro Val Glu Val Gly Gly Ala
-15             -10                      -5                    1

GGG CCC CCG CCA ATC CAG GAC GGT GAG TTC ACG TTC CTG TTG CCG GCG              207
Gly Pro Pro Pro Ile Gln Asp Gly Glu Phe Thr Phe Leu Leu Pro Ala
              5                 10                  15

GGG AGG AAG CAG TGT TTC TAC CAG TCC GCG CCG GCC AAC GCA AGC CTC              255
Gly Arg Lys Gln Cys Phe Tyr Gln Ser Ala Pro Ala Asn Ala Ser Leu
         20                  25                  30

GAG ACC GAA TAC CAG GTG ATC GGA GGT GCT GGA CTG GAC GTG GAC TTC              303
Glu Thr Glu Tyr Gln Val Ile Gly Gly Ala Gly Leu Asp Val Asp Phe
     35                  40                  45

ACG CTG GAG AGC CCT CAG GGC GTG CTG TTG GTC AGC GAG TCC CGC AAG              351
Thr Leu Glu Ser Pro Gln Gly Val Leu Leu Val Ser Glu Ser Arg Lys
 50              55                  60                      65

GCT GAT GGG GTA CAC ACG GTG GAG CCA ACG GAG GCC GGG GAC TAC AAG              399
Ala Asp Gly Val His Thr Val Glu Pro Thr Glu Ala Gly Asp Tyr Lys
                 70                  75                  80

CTG TGC TTT GAC AAC TCC TTC AGC ACC ATC TCC GAG AAG CTG GTG TTC              447
Leu Cys Phe Asp Asn Ser Phe Ser Thr Ile Ser Glu Lys Leu Val Phe
             85                  90                  95

TTT GAA CTG ATC TTT GAC AGC CTC CAG GAT GAC GAG GAG GTC GAA GGA              495
Phe Glu Leu Ile Phe Asp Ser Leu Gln Asp Asp Glu Glu Val Glu Gly
         100                 105                 110

TGG GCA GAG GCT GTG GAG CCC GAG GAG ATG CTG GAT GTT AAA ATG GAG              543
Trp Ala Glu Ala Val Glu Pro Glu Glu Met Leu Asp Val Lys Met Glu
     115                 120                 125

GAC ATC AAG GAG TCC ATT GAG ACC ATG CGG ACC CGG CTG GAG CGC AGC              591
Asp Ile Lys Glu Ser Ile Glu Thr Met Arg Thr Arg Leu Glu Arg Ser
130              135                 140                     145

ATC CAG ATG CTC ACG CTA CTG CGG GCC TTC GAG GCA CGT GAC CGC AAC              639
Ile Gln Met Leu Thr Leu Leu Arg Ala Phe Glu Ala Arg Asp Arg Asn
             150                 155                 160

CTG CAA GAG GGC AAC TTG GAG CGG GTC AAC TTC TGG TCA GCT GTC AAC              687
Leu Gln Glu Gly Asn Leu Glu Arg Val Asn Phe Trp Ser Ala Val Asn
         165                 170                 175

GTG GCG GTG CTG CTG CTG GTG GCT GTG CTG CAG GTC TGC ACG CTC AAG              735
Val Ala Val Leu Leu Leu Val Ala Val Leu Gln Val Cys Thr Leu Lys
     180                 185                 190

CGC TTC TTC CAG GAC AAG CGC CCG GTG CCC ACG TAGCCCCTGC CATGGAAGGA           788
Arg Phe Phe Gln Asp Lys Arg Pro Val Pro Thr
     195                 200             205

AGAACGGGAC AAAGGAGGGG CAGCAGGGTG TGTGCATATG AGACTTGGGG GTCCCTCCCC            848

AATTTTAGTT TCCTGCCAAA ACGGGAGTGT GCAGTCAGGG CCTGCGGTCT GGCCCCATGA            908

GTCTCCTTCC GTCCTCAGCG GGCAGGGAAC ACCTCTGGCT TGTAGAAGGG ACGGCTCAGT            968

GGCTGCACCG ACGGTCCTGG AAATCTCACA TGGTGGGCAC TGCAGCGTTG AACGTGAGC            1028

CTCGGATTTC CTGGCCCCTC TACTGTAAAT GTGCCTTAGC CTAAGCCTCC CATCCTGTGT           1088

TAGCGTTGCC TGGTGCGGGG CAGGGCCTAA CAAGGAAACC TGGGCCCTCC AAGCCAGGTT           1148

GAGGTCTGGT AACAGAATGC CAGGAAGGGG GCCTGGAAGA CCACCTGCCC CGGCCCCTCT           1208

CCTGCAGGGG CCCCACACAG GCATGAGGGA TGGCCCGGCC AAAGTCTAGG CAGAAGCCTC           1268

CTATAACAAA GGGTGGTGTG GCCTGGGCAT TGGAG                                     1303
```

( 2 ) INFORMATION FOR SEQ ID NO:2:

( i ) SEQUENCE CHARACTERISTICS:
        ( A ) LENGTH: 227 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Met Ala Ala Gly Ala Ala Leu Ala Leu Ala Leu Trp Leu Leu Met
-23         -20                 -15                 -10
Pro Pro Val Glu Val Gly Gly Ala Gly Pro Pro Pro Ile Gln Asp Gly
         -5              1               5
Glu Phe Thr Phe Leu Leu Pro Ala Gly Arg Lys Gln Cys Phe Tyr Gln
 10              15              20                       25
Ser Ala Pro Ala Asn Ala Ser Leu Glu Thr Glu Tyr Gln Val Ile Gly
             30              35                         40
Gly Ala Gly Leu Asp Val Asp Phe Thr Leu Glu Ser Pro Gln Gly Val
         45              50              55
Leu Leu Val Ser Glu Ser Arg Lys Ala Asp Gly Val His Thr Val Glu
         60              65              70
Pro Thr Glu Ala Gly Asp Tyr Lys Leu Cys Phe Asp Asn Ser Phe Ser
 75              80              85
Thr Ile Ser Glu Lys Leu Val Phe Phe Glu Leu Ile Phe Asp Ser Leu
 90              95              100                     105
Gln Asp Asp Glu Glu Val Glu Gly Trp Ala Glu Ala Val Glu Pro Glu
             110             115                     120
Glu Met Leu Asp Val Lys Met Glu Asp Ile Lys Glu Ser Ile Glu Thr
         125             130             135
Met Arg Thr Arg Leu Glu Arg Ser Ile Gln Met Leu Thr Leu Leu Arg
         140             145             150
Ala Phe Glu Ala Arg Asp Arg Asn Leu Gln Glu Gly Asn Leu Glu Arg
     155             160             165
Val Asn Phe Trp Ser Ala Val Asn Val Ala Val Leu Leu Leu Val Ala
170             175             180                     185
Val Leu Gln Val Cys Thr Leu Lys Arg Phe Phe Gln Asp Lys Arg Pro
             190             195             200
Val Pro Thr
```

( 2 ) INFORMATION FOR SEQ ID NO:3:

( i ) SEQUENCE CHARACTERISTICS:
        ( A ) LENGTH: 1251 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i i ) IMMEDIATE SOURCE:
        ( B ) CLONE: muST2-lig ( i x ) FEATURE:
        ( A ) NAME/KEY: mat_peptide
        ( B ) LOCATION: 64..672

( i x ) FEATURE:
        ( A ) NAME/KEY: CDS
        ( B ) LOCATION: 1..675

( i x ) FEATURE:
    ( A ) NAME/KEY: sig_peptide
    ( B ) LOCATION: 1..63

( x i ) SEQUENCE DESCRIPTION: SEQ ID NO:3:

```
GCC GGC GCG GCC GTA GCA CTG GCC CTG TGG CTA CTC CTG CCA GCA GTA   48
Ala Gly Ala Ala Val Ala Leu Ala Leu Trp Leu Leu Leu Pro Ala Val
-21 -20              -15                      -10

GGA GTG GGA GAG GCA GGG CCG CCG CCT ATC CAG GAC GGC GAG TTC ACA   96
Gly Val Gly Glu Ala Gly Pro Pro Pro Ile Gln Asp Gly Glu Phe Thr
 -5              1               5                       10

TTT CTG CTT CCC GCC GGG AGA AAG CAG TGT TTC TAT CAG TCC GCA CCG  144
Phe Leu Leu Pro Ala Gly Arg Lys Gln Cys Phe Tyr Gln Ser Ala Pro
             15                  20                  25

GCC AAT GCT AGT CTT GAG ACC GAG TAC CAG GTG ATC GGA GGT GCT GGG  192
Ala Asn Ala Ser Leu Glu Thr Glu Tyr Gln Val Ile Gly Gly Ala Gly
         30                  35                  40

CTG GAC GTG GAC TTC ACC TTG GAG AGC CCT CAG GGT GTG CTG TTG GTC  240
Leu Asp Val Asp Phe Thr Leu Glu Ser Pro Gln Gly Val Leu Leu Val
         45                  50                  55

AGT GAG TCT CGA AAG GCT GAT GGG GTA CAC ACG GTG GAG CCT ACT GAG  288
Ser Glu Ser Arg Lys Ala Asp Gly Val His Thr Val Glu Pro Thr Glu
 60                  65                  70                  75

GCC GGA GAC TAC AGG CTG TGC TTT GAC AAC TCC TTC AGC ACC ATC TCA  336
Ala Gly Asp Tyr Arg Leu Cys Phe Asp Asn Ser Phe Ser Thr Ile Ser
             80                  85                  90

GAA AAG CTT GTG TTC TTT GAG CTC ATC TTT GAC AGC TTC CAA GAT GAG  384
Glu Lys Leu Val Phe Phe Glu Leu Ile Phe Asp Ser Phe Gln Asp Glu
                 95                 100                 105

GAG GAG GTA GAA GGT TGG GCG GAG GCT GTG GAG CCA GAA GAG ATG CTT  432
Glu Glu Val Glu Gly Trp Ala Glu Ala Val Glu Pro Glu Glu Met Leu
            110                 115                 120

GAT GTC AAA ATG GAA GAC ATC AAG GAA TCC ATA GAG ACC ATG AGG ACC  480
Asp Val Lys Met Glu Asp Ile Lys Glu Ser Ile Glu Thr Met Arg Thr
            125                 130                 135

CGG CTG GAA CGG AGC ATC CAG ATG CTC ACT CTC CTC CGA GCC TTT GAG  528
Arg Leu Glu Arg Ser Ile Gln Met Leu Thr Leu Leu Arg Ala Phe Glu
140                 145                 150                 155

GCT CGT GAT CGA AAT CTT CAA GAA GAC AAC CTG GAG CGG GTC AAC TTC  576
Ala Arg Asp Arg Asn Leu Gln Glu Asp Asn Leu Glu Arg Val Asn Phe
                160                 165                 170

TGG TCA GCT GCC AAT GTG GCT GTG TTG CTG CTG GTG GCT GTC CTG CAA  624
Trp Ser Ala Ala Asn Val Ala Val Leu Leu Leu Val Ala Val Leu Gln
            175                 180                 185

GTC TGC ACA CTC AAG CGC TTC TTC CAT GAC AAG CGC CCT GTA CCC ACG  672
Val Cys Thr Leu Lys Arg Phe Phe His Asp Lys Arg Pro Val Pro Thr
            190                 195                 200
```

TAGCCCCTGC CACAGAGGAT GAGGGCAGCG GTGTGTGAC TTGCTGGACA CCTCCCAGAC 732
TCAGATGAGA CACTACATAG TTGGGTCCTT AGCAGTGGCC CCATGTGTCT CCCTTCCTCA 792
GTGACCAGGG AGTGCCAATG GCTCACAGAC CCCTCGGAAG GGGGAGGGCT CAGCGACTGT 852
GCCTGTTCCT TGGAGGGTGG AAGTGCTGGG CGCAGCAGTG TGGGGACACT GCTCTTGGAT 912
GCCCTGGCTT TCTCCTGAAA TCGTGCCTTA GCTTCAGTCT TGCAGCTATC AGGATGGGGT 972
GAAGCTGTGG TGCTGCCCCC CACCCTCCAA CTAGACACCC CAACTGCAAT GTCTCTGCTC 1032
TCCTCCTGGG GTAAGCCTAC TTCACTAGGG TCTGGGAAGG AGACACATCT GCAGAGTTCT 1092
TGCCAGGACA GTCACTTTTA TTTGAAAGGA AGGAGCCCTG GCCCCTTGGC CCAGAGGGGA 1152
GCCAGCTAGT AGGTGGTTTG GGAGAGGCCC CTTCCTTCTC TCTGGGTGCA GGGCCTCAGA 1212

GAAGGCTGGC CCATGAGCCT CAAGGAACAG AGGGCATTT 1251

( 2 ) INFORMATION FOR SEQ ID NO:4:

( i ) SEQUENCE CHARACTERISTICS:
        ( A ) LENGTH: 224 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ala | Gly | Ala | Ala | Val | Ala | Leu | Ala | Leu | Trp | Leu | Leu | Leu | Pro | Ala | Val |
|---|---|---|---|---|---|---|---|---|---|---|---|---|---|---|---|
| -21 | -20 | | | | -15 | | | | | -10 | | | | | |
| Gly | Val | Gly | Glu | Ala | Gly | Pro | Pro | Pro | Ile | Gln | Asp | Gly | Glu | Phe | Thr |
| -5 | | | | | 1 | | | | 5 | | | | | 10 | |
| Phe | Leu | Leu | Pro | Ala | Gly | Arg | Lys | Gln | Cys | Phe | Tyr | Gln | Ser | Ala | Pro |
| | | | 15 | | | | 20 | | | | | | 25 | | |
| Ala | Asn | Ala | Ser | Leu | Glu | Thr | Glu | Tyr | Gln | Val | Ile | Gly | Gly | Ala | Gly |
| | | 30 | | | | | 35 | | | | | 40 | | | |
| Leu | Asp | Val | Asp | Phe | Thr | Leu | Glu | Ser | Pro | Gln | Gly | Val | Leu | Leu | Val |
| | | 45 | | | | 50 | | | | | 55 | | | | |
| Ser | Glu | Ser | Arg | Lys | Ala | Asp | Gly | Val | His | Thr | Val | Glu | Pro | Thr | Glu |
| 60 | | | | | 65 | | | | | 70 | | | | | 75 |
| Ala | Gly | Asp | Tyr | Arg | Leu | Cys | Phe | Asp | Asn | Ser | Phe | Ser | Thr | Ile | Ser |
| | | | | 80 | | | | | 85 | | | | | 90 | |
| Glu | Lys | Leu | Val | Phe | Phe | Glu | Leu | Ile | Phe | Asp | Ser | Phe | Gln | Asp | Glu |
| | | | 95 | | | | | 100 | | | | | 105 | | |
| Glu | Glu | Val | Glu | Gly | Trp | Ala | Glu | Ala | Val | Glu | Pro | Glu | Glu | Met | Leu |
| | | 110 | | | | | 115 | | | | | 120 | | | |
| Asp | Val | Lys | Met | Glu | Asp | Ile | Lys | Glu | Ser | Ile | Glu | Thr | Met | Arg | Thr |
| | 125 | | | | | 130 | | | | | 135 | | | | |
| Arg | Leu | Glu | Arg | Ser | Ile | Gln | Met | Leu | Thr | Leu | Leu | Arg | Ala | Phe | Glu |
| 140 | | | | | 145 | | | | | 150 | | | | | 155 |
| Ala | Arg | Asp | Arg | Asn | Leu | Gln | Glu | Asp | Asn | Leu | Glu | Arg | Val | Asn | Phe |
| | | | | 160 | | | | | 165 | | | | | 170 | |
| Trp | Ser | Ala | Ala | Asn | Val | Ala | Val | Leu | Leu | Leu | Val | Ala | Val | Leu | Gln |
| | | | 175 | | | | | 180 | | | | | 185 | | |
| Val | Cys | Thr | Leu | Lys | Arg | Phe | Phe | His | Asp | Lys | Arg | Pro | Val | Pro | Thr |
| | | 190 | | | | | 195 | | | | | 200 | | | |

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i i ) IMMEDIATE SOURCE:
        ( B ) CLONE: FLAG peptide ( x i ) SEQUENCE DESCRIPTION: SEQ ID NO:5:

| Asp | Tyr | Lys | Asp | Asp | Asp | Asp | Lys |
|---|---|---|---|---|---|---|---|
| 1 | | | | 5 | | | |

CYTOKINE THAT BINDS ST2

BACKGROUND OF THE INVENTION

The protein variously known as ST2, T1, or Fit-1 is a member of the immunoglobulin superfamily. This superfamily, defined by certain conserved amino acid sequences, comprises proteins exhibiting diverse functions that include antigen recognition, cell adhesion, and signal transduction (reviewed in Williams and Barclay, *Annu. Rev. Immunol.* 6:381, 1988).

Cloning of murine T1 cDNA was described by Klemenz et al. (*Proc. Natl. Acad. Sci. USA* 86:5708, 1989). The predicted amino acid sequence of the T1 protein was reported to be similar to that of human carcinoembryonic antigen, a tumor marker that is a member of the immunoglobulin gene superfamily. The encoded amino acid sequence included an N-terminal signal peptide, but no transmembrane region, suggesting that the T1 protein was secreted rather than membrane-bound.

Cloning of cDNA encoding the same murine protein, which was designated ST2, was reported by Tominaga (*FEBS LETTERS* 258:301, 1989). The encoded ST2 protein was determined to be a member of the immunoglobulin superfamily, and to be especially similar to the extracellular domain of the mouse type I interleukin-1 receptor.

DNA encoding a membrane-bound form of the mouse ST2 protein has been isolated and designated ST2L (Yanagisawa et al., *FEBS LETTERS* 318:83, 1993). The encoded protein contains the signal peptide and extracellular domain of the previously-identified ST2 protein, but comprises additional 3' sequence encoding a transmembrane region and a cytoplasmic domain. The amino acid sequences of ST2L and murine type I IL-1 receptor were found to be 28% identical over the whole protein, 25% identical in the extracellular domains, and 38% identical in the cytoplasmic domains. Regarding murine type II IL-1 receptor, the amino acid sequence of the extracellular domain was 23% identical to that of ST2/ST2L, while the cytoplasmic domain exhibited no significant homology to the cytoplasmic domain of ST2L.

Human ST2 cDNA and genomic clones have been isolated (Tominaga et al. *Biochimica et Biophysica Acta* 1171:215, 1992). The amino acid sequence encoded by the cDNA includes a signal peptide but apparently lacks any transmembrane region. No membrane-bound human ST2 protein was reported. The DNA and predicted amino acid sequences of human ST2 were said to be substantially similar to those of overlapping regions of human interleukin-1 receptor (both type I and type II; McMahan et al., *EMBO J.* 10:2821., 1991); the B16R protein of vaccinia virus (Goebel et al., *Virology* 179:247, 1990), Cek 2 of *Drosophila* (a protein tyrosine kinase; Pasquale, *Proc. Natl. Acad. Sci. USA* 87:5812, 1990); and klg (a chicken kinase-like protein; Chou and Hayman, *Proc. Natl. Acad. Sci. USA* 88:4897, 1991).

Werenskiold (*Eur. J. Biochem.* 204:1041, 1992) further characterizes a recombinant secreted form of the murine T1 glycoprotein. The possibility that T1 plays a role in neoplastic transformation or cell proliferation was suggested.

DNAs encoding a membrane-bound form and a naturally occurring secreted (soluble) form of the rat homolog of the ST2 protein have been isolated (Bergers et al., *EMBO J.* 13:1176, 1994). The membrane-bound rat protein is most closely related to the type I IL-1 receptor. The two forms of the protein are expressed from different promoters, allowing differential regulation. Expression of the mouse gene in different tissues at various developmental stages was investigated. The mRNA encoding the membrane-bound form was found to be expressed more abundantly than mRNA for the secreted form in fetal liver and in adult lung and hematopoietic tissues. The transcript for the secreted form predominated in fibroblasts and mammary epithelial cells.

As discussed above, ST2 is structurally similar to interleukin-1 receptors. In addition, the St2 locus is very tightly linked to the Il-lr1 and Il-lr2 loci on mouse chromosome 1 (Tominaga et al., *Biochimica et Biophysica Acta* 1090: 1, 1991). Consequently, the hypothesis that interleukin-1 will bind to ST2 has been presented by several investigators (Tominaga et al., 1992, supra; Yanagisawa et al., 1993, supra; Bergers et al., supra). The search for a ligand for ST2 thus was initially focused on interleukin-1.

SUMMARY OF THE INVENTION

The present invention provides a novel cytokine designated ST2 ligand that binds to the protein known as ST2. Both soluble and membrane-bound forms of ST2 ligand are disclosed herein. The present invention also provides isolated DNA encoding ST2 ligand proteins, expression vectors comprising the isolated DNA, and a method for producing ST2 ligand by cultivating host cells containing the expression vectors under conditions appropriate for expression of the ST2 ligand protein. Antibodies directed against ST2 ligand are also disclosed. The ligand binds to certain types of lymphoma cells, and thus may be used, to deliver diagnostic or therapeutic agents thereto.

DETAILED DESCRIPTION OF THE INVENTION cDNA encoding a novel protein that binds to the protein known as ST2 has been isolated in accordance with the present invention. ST2 is a member of the immunoglobulin superfamily, and exhibits structural similarity to interleukin-1 receptors, as discussed above. Surprisingly, the novel ST2 ligand is not structurally similar to the interleukin-1 proteins.

Expression vectors comprising the ST2 ligand cDNA are provided, as well as methods for producing recombinant ST2 ligand polypeptides by cultivating host cells containing the expression vectors under conditions appropriate for expression of ST2 ligand, then recovering the expressed ligand. Purified ST2 ligand protein is also encompassed by the present invention, including soluble forms of the protein comprising the extracellular domain.

The present invention also provides ST2 ligand or immunogenic fragments thereof that may be employed as immunogens to generate antibodies specific thereto. In one embodiment, the antibodies are monoclonal antibodies.

Prior to the present invention, interleukin-1 proteins were considered to be likely candidates for ST2 ligands (Tominaga et al., 1992, supra; Yanagisawa et al., 1993, supra; and Bergers et al., supra). However, soluble human ST2 (in the form of a fusion protein) failed to bind human IL-1α, IL-1β, or IL-1 receptor antagonist proteins, as described in example 2 below. Thus, a search for putative ST2 ligand proteins began.

Human ST2 ligand eDNA was isolated using a direct expression cloning technique, as described in example 3. *E. coli* DH10B cells transformed with a recombinant vector containing the human ST2 ligand cDNA were deposited with the American Type Culture Collection on June 10, 1994, and assigned accession no. ATCC 69645. The deposit was made under the terms of the Budapest Treaty. The recombinant vector comprised the ST2 ligand cDNA inserted into the SalI site of a cloning vector designated GEMBL18.

The DNA sequence and encoded amino acid sequence of this human ST2 ligand cDNA are presented in SEQ ID NO:1 and SEQ ID NO:2. The encoded protein comprises (from N- to C-terminus) a signal peptide (amino acids −23 to −1 of SEQ ID NO:2), an extracellular domain (amino acids 1 to 171), a transmembrane region (amino acids 172 to 192) and a short cytoplasmic domain (amino acids 193 to 204). Particular embodiments of the present invention are directed to an isolated DNA sequence comprising the sequence of nucleotides 88 to 771 of SEQ ID NO:1 or nucleotides 157 to 771 of SEQ ID NO: 1.

Comparison of both the nucleotide and encoded amino acid sequences of the human ST2 ligand cDNA clone with sequence databanks showed that the sequence of the ST2 ligand was unique. The amino acid sequences identified in this search as being most structurally similar to the ST2 ligand were an uncharacterized open reading frame (ORF) from Saccharomyces chromosome 1 (Genbank no. L22015) and a protein known as EMP24, which is a component of yeast endosomes (Singer-Kruger et al., *J. Biol. Chem.* 268: 14376, 1993). The identity between all three sequences, which appears to extend throughout their entire length, is 23%.

Surprisingly, the ST2 ligand exhibits no significant homology to interleukin-1 proteins (either α or β), in spite of the structural similarity of ST2 to interleukin-1 receptors, as discussed above. The fact that the cloned DNA encodes a membrane bound protein is also surprising. IL-1 proteins are soluble, which supported a prediction that an ST2 ligand protein would be soluble as well, given the structural similarities between ST2 and IL-1 receptors.

Mouse ST2 ligand DNA was isolated by cross-species hybridization, as described in example 6. The DNA and encoded amino acid sequences of this mouse ST2 ligand DNA are presented in SEQ ID NO:3 and SEQ ID NO:4. The absence of an initiation codon indicates that this mouse ST2 ligand DNA is truncated at the 5' end. The protein of SEQ ID NO:4 comprises a partial signal peptide (amino acids −21 to −1 ), an extracellular domain (amino acids 1 to 170), a transmembrane region (amino acids 171 to 191), and a short cytoplasmic domain (amino acids 192 to 203). One DNA of the present invention comprises nucleotides 64 to 675 of SEQ ID NO:3. Alignment with the human ST2 ligand amino acid sequence suggested that the encoded murine ST2 ligand lacked the first three amino acids of the signal peptide, but contained a partial signal peptide and the complete mature protein. DNA that provided a complete signal peptide-encoding sequence (including an initiation codon) was added to this murine DNA as described in example 5.

Human and mouse ST2 ligand are within the scope of the present invention, as are ST2 ligand proteins derived from other mammalian species, including but not limited to rat, bovine, porcine, or various non-human primates. Various types of cells or cell lines derived from other mammalian species can be screened for the ability to bind ST2. cDNA libraries prepared from such cells may be employed in a direct expression cloning procedure (e.g., as described in example 3) to isolate positive clones. Also, mRNAs isolated from various cell lines can be screened in Northern blots to determine a suitable source of mRNA for use in cloning an ST2 ligand gene.

The term "ST2 ligand" as used herein refers to a genus of polypeptides that are capable of binding ST2. As used herein, the term "ST2 ligand" includes membrane-bound proteins (comprising an extracellular domain, a transmembrane region, and a cytoplasmic domain) as well as truncated proteins that retain the ST2-binding property. Such truncated proteins include, for example, soluble ST2 ligand comprising only the extracellular (receptor binding) domain.

One embodiment of the present invention provides soluble ST2 ligand polypeptides. Soluble ST2 ligand polypeptides comprise all or part of the extracellular domain of a native ST2 ligand but lack the transmembrane region that would cause retention of the polypeptide on a cell membrane. When initially synthesized, soluble ST2 ligand polypeptides advantageously comprise the native (or a heterologous) signal peptide to promote secretion, but the signal peptide is cleaved upon secretion of ST2 ligand from the cell. The soluble ST2 ligand polypeptides that may be employed retain the ability to bind the ST2 receptor. Soluble ST2 ligand may also include part of the transmembrane region or part of the cytoplasmic domain or other sequences, provided that the soluble ST2 ligand protein is capable of being secreted.

Soluble ST2 ligand may be identified (and distinguished from its non-soluble membrane-bound counterparts) by separating intact cells which express the desired protein from the culture medium, e.g., by centrifugation, and assaying the medium (supenatant) for the presence of the desired protein. The presence of ST2 ligand in the medium indicates that the protein was secreted from the cells and thus is a soluble form of the desired protein. Soluble ST2 ligand may be a naturally-occurring form of this protein.

The use of soluble forms of ST2 ligand is advantageous for certain applications. Purification of the proteins from recombinant host cells is facilitated, since the soluble proteins are secreted from the cells. Further, soluble proteins are generally more suitable for intravenous administration.

Examples of soluble ST2 ligand polypeptides include those comprising the entire extracellular domain of a native ST2 ligand protein. One such polypeptide is a soluble human ST2 ligand comprising amino acids 1 through 171 of SEQ ID NO:2. When initially expressed within a host cell, the soluble protein may additionally comprise one of the heterologous signal peptides described below that is functional within the host cells employed. Alternatively, the protein may comprise the native signal peptide, such that the ST2 ligand comprises amino acids −23 through 171 of SEQ ID NO:2. An example of a soluble murine ST2 ligand comprises amino acids 1 through 170 of SEQ ID NO:4. When initially expressed, the soluble murine ST2 ligand advantageously comprises a signal peptide, such as one of the signal peptides described below. DNA sequences encoding soluble ST2 ligand polypeptides are encompassed by the present invention. Particular embodiments of the present invention are directed to isolated DNA sequences encoding a soluble human ST2 ligand, wherein said DNA sequences comprise a nucleotide sequence selected from the group consisting of nucleotides 88 to 669 of SEQ ID NO:1 and nucleotides 157 to 669 of SEQ ID NO:1.

Truncated ST2 ligands, including soluble polypeptides, may be prepared by any of a number of conventional techniques. A desired DNA sequence may be chemically synthesized using known techniques. DNA fragments also may be produced by restriction endonuclease digestion of a full length cloned DNA sequence, and isolated by electrophoresis on agarose gels. Oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence. Linkers containing restriction endonuclease cleavage site(s) may be employed to insert the desired DNA fragment into an expression vector. The well known polymerase chain reaction procedure also may be employed to isolate a DNA sequence encoding a desired protein fragment. Oligonucleotides that define the termini of the desired fragment are employed as primers in the PCR. As a further alternative, known mutagenesis techniques may be employed to insert a stop codon at a desired point, e.g., immediately downstream of the codon for the last amino acid of the extracellular domain.

Regarding the foregoing discussion of signal peptides and the various domains of the ST2 ligand proteins, the skilled artisan will recognize that the above-described boundaries of such regions of the proteins are approximate. For example, although computer programs that predict the site of cleavage of a signal peptide are available, cleavage can occur at sites other than those predicted. Further, it is recognized that a protein preparation can comprise a mixture of protein molecules having different N-terminal amino acids, due to cleavage of the signal peptide at more than one site. In addition, the exact boundaries of a transmembrane region may differ from that predicted by a computer program. Post-translational processing, which can vary according to the particular expression system employed, may also yield proteins having differing N- or C-terminal amino acids. Such variants that retain the desired biological activity are included among the ST2 ligand polypeptides of the present invention.

The present invention provides purified ST2 ligand polypeptides, both recombinant and non-recombinant. Variants and derivatives of native ST2 ligand proteins that retain the desired biological activity (e.g., the ability to bind ST2) are also within the scope of the present invention. ST2 ligand variants may be obtained by mutations of nucleotide sequences coding for native ST2 ligand polypeptides. An ST2 ligand variant, as referred to herein, is a polypeptide substantially homologous to a native ST2 ligand, but which has an amino acid sequence different from that of a native ST2 ligand because of one or more deletions, insertions or substitutions.

The variant amino acid sequence preferably is at least 80% identical to a native ST2 ligand amino acid sequence, most preferably at least 90% identical. The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981 ). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure,* National Biomedical Research Foundation, pp. 353–358, 1979; (2) a penalty of 3.0 for each gap and an additional 0.10 penalty for each symbol in each gap; and (3) no penalty for end gaps.

DNA encoding such variants is provided by the present invention as well. Such DNA sequences preferably are at least 80% identical to a native ST2 ligand DNA sequence, most preferably at least 90% identical. The percent identity may be determined using known computer programs, such as the above-described GAP program.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981 ); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462, which are incorporated by reference herein.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other conservative substitutions, for example, substitutions of entire regions having similar hydrophobicity characteristics, are well known.

ST2 ligands also may be modified to create ST2 ligand derivatives by forming covalent or aggregative conjugates with other chemical moieties, such as glycosyl groups, lipids, phosphate, acetyl groups and the like. Covalent derivatives of ST2 ligands may be prepared by linking the chemical moieties to functional groups on ST2 ligand amino acid side chains, or at the N-terminus or C-terminus of an ST2 ligand polypeptide or the extracellular domain thereof. Other derivatives of ST2 ligand within the scope of this invention include covalent or aggregative conjugates of ST2 ligands with other proteins or polypeptides, e.g., N-terminal or C-terminal fusions produced by recombinant DNA technology. For example, the conjugate may comprise a heterologous signal or leader polypeptide sequence (e.g. the α-factor leader of Saccharomyces) at the N-terminus of a ST2 ligand polypeptide. The signal or leader peptide co-translationally or post-translationally directs transfer of the conjugate from its site of synthesis to a site inside or outside of the cell membrane or cell wall.

ST2 ligand polypeptide fusions can comprise peptides added to facilitate purification and identification of ST2 ligand. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK) (SEQ ID NO:5), which is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. In one embodiment of the present invention, the peptide of SEQ ID NO:5 is fused to a soluble ST2 ligand. The peptide preferably is fused to the C-terminus of the extracellular domain of an ST2 ligand.

The present invention further includes ST2 ligand polypeptides with or without associated native-pattern glycosylation. ST2 ligand expressed in yeast or mammalian expression systems (e.g., COS-7 cells) may be similar to or significantly different from a native ST2 ligand polypeptide in molecular weight and glycosylation pattern, depending upon the choice of expression system. Expression of ST2 ligand polypeptides in bacterial expression systems, such as *E. coli,* provides non-glycosylated molecules.

N-glycosylation sites in the ST2 ligand extracellular domain can be modified to preclude glycosylation. N-glycosylation sites in eukaryotic polypeptides are characterized by an amino acid triplet Asn-X-Y, wherein X is any amino acid except Pro and Y is Ser or Thr. The human ST2 ligand protein comprises one such triplet at amino acids 30–32 of SEQ ID NO:2. The murine ST2 ligand protein comprises one such triplet, at amino acids 29–31 of SEQ ID NO:4. Appropriate modifications to the nucleotide sequence encoding this triplet will result in substitutions, additions or deletions that prevent attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding cysteine residues that are not essential for biological activity can be altered to cause the cysteine residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. Human ST2 ligand contains four KEX2 protease processing sites, at amino acids 19–20, 64–65, 193–194, and 199–200 of SEQ ID NO:2. Murine ST2 ligand contains four KEX2 protease processing sites, at amino acids 18–19, 63–64, 192–193, and 198–199 of SEQ ID NO:4.

Naturally occurring ST2 ligand variants are also encompassed by the present invention. Examples of such variants are proteins that result from alternative mRNA splicing events or from proteolytic cleavage of the ST2 ligand protein, wherein the ST2binding property is retained. Alternative splicing of mRNA may yield a truncated but biologically active ST2 ligand protein, such as a naturally occurring soluble form of the protein, for example. Variations attributable to proteolysis include, for example, differences in the N- or C-termini upon expression in different types of host cells, due to proteolytic removal of one or more terminal amino acids from the ST2 ligand protein (e.g., from 1-5 terminal amino acids).

Nucleic acid sequences within the scope of the present invention include isolated DNA and RNA sequences that hybridize to the native ST2 ligand nucleotide sequences disclosed herein under moderately or highly stringent conditions, and which encode biologically active ST2 ligand. Moderate stringency hybridization conditions refer to conditions described in, for example, Sambrook et al., *Molecular Cloning: A Laboratory Manual,* 2 ed. Vol. 1, pp. 1.101–104, Cold Spring Harbor Laboratory Press, (1989). Conditions of moderate stringency, as defined by Sambrook et al., include use of a prewashing solution of 5×SSC, 0.5% SDS, 1.0 mM EDTA (pH 8.0), hybridization at about 55° C. in 5×SSC overnight, followed by washing at 50°–55° C. in 2×SSC, 0.1% SDS. Highly stringent conditions include higher temperatures of hybridization and washing. The skilled artisan will recognize that the temperature and wash solution salt concentration may be adjusted as necessary according to factors such as the length of the probe. In one embodiment, highly stringent conditions include hybridization at 68° C followed by washing in 0.1×SSC/0.1% SDS at 63°–68° C.

Due to the known degeneracy of the genetic code, wherein more than one codon can encode the same amino acid, a DNA sequence may vary from that presented. in SEQ ID NO:1 or 3, and still encode an ST2 ligand protein having the amino acid sequence of SEQ ID NO:2 or 4, respectively. Such variant DNA sequences may result from silent mutations that occur during PCR amplification, for example. Alternatively, the variant sequence may be the product of deliberate mutagenesis of a native sequence.

The present invention thus provides isolated DNA sequences encoding biologically active ST2 ligand, selected from: (a) DNA derived from the coding region of a native mammalian ST2 ligand gene (e.g., DNA comprising the coding region of the nucleotide sequence presented in SEQ ID NO:1 or 3); (b) DNA capable of hybridization to a DNA of (a) under moderately or highly stringent conditions and which encodes an ST2 ligand capable of binding ST2; and (c) DNA which is degenerate as a result of the genetic code to a DNA defined in (a) or (b) and which encodes an ST2 ligand capable of binding ST2. The ST2 ligand proteins encoded by such DNA sequences are encompassed by the present invention.

Examples of ST2 ligand proteins encoded by DNA that varies from the native DNA sequence of SEQ ID NO:1 or 3, wherein the variant DNA will hybridize to the native DNA sequence under moderately or highly stringent conditions, include, but are not limited to, ST2 ligand fragments (soluble or membrane-bound) and ST2 ligand proteins comprising inactivated N-glycosylation site(s), inactivated KEX2 protease processing site(s), or conservative amino acid substitution(s), as described above. ST2 ligand proteins encoded by DNA derived from other mammalian species, wherein the DNA will hybridize to the human DNA of SEQ ID NO:1 or the mouse DNA of SEQ ID NO:3, are also encompassed.

Variants possessing the requisite ability to bind ST2 may be identified by any suitable assay. Biological activity of an ST2 ligand may be determined, for example, by competition for binding to the ligand binding domain of ST2 (i.e., competitive binding assays).

Competitive binding assays can be performed using standard methodology. For example, a native ST2 ligand can be used to compete with an ST2 ligand variant for binding to cell surface-bound ST2. The native ligand is labeled with a detectable reagent by a method that preserves the biological activity thereof. Qualitative results can be obtained by competitive autoradiographic plate binding assays, or Scatchard plots may be utilized to generate quantitative results. Another type of competitive binding assay utilizes an ST2/Fc fusion protein, and intact cells expressing ST2 ligand. The ability of an ST2 ligand variant to compete with the ligand on the cell surface for binding of ST2/Fc is tested in this assay. A labeled antibody that binds the Fc moiety (e.g., a radioiodinated mouse anti-human IgG directed against the Fc region) is employed to detect ST2/Fc fusion protein that has bound to the cells.

Another type of binding assay uses a soluble human ST2 ligand/Fc fusion protein and intact cells expressing cell surface ST2. Binding of the ligand/Fc fusion protein to the cells is detected using a labeled antibody that binds the Fc moiety.

Binding can also be determined using a BIAcore Processing Unit (Pharmacia Biosensor). One such procedure involves chemically attaching goat anti-human IgG to the chip of the Biosensor, then binding ST2/Fc to the immobilized goat anti-human IgG. Next, a solution containing an ST2 ligand protein flows over the chip, and binding of the ligand is detected by a change in the mass of the molecules bound to the chip. Dissociation of the ligand from the receptor also can be detected. An alternative procedure involves attaching goat anti-human IgG followed by soluble ST2 ligand/Fc to the chip, then exposing a solution containing ST2 to the immobilized ligand.

The ST2 ligand of the present invention can be used in a binding assay to detect cells expressing ST2. For example, ST2 ligand or an extracellular domain or a fragment thereof can be labeled with a detectable moiety, such as a radionuclide, an enzyme that can catalyze a colorometric or fluorometric reaction, biotin or avidin. Cells to be tested for ST2 expression are contacted with the labeled ST2 ligand. After incubation, unbound labeled ST2 ligand is removed and binding is measured using the detectable moiety. Alternatively, the cells are first contacted with unlabeled ST2 ligand/Fc, followed by a labeled antibody that will bind the Fc moiety.

The ST2 ligand proteins disclosed herein also may be employed to measure the biological activity of ST2 proteins in terms of binding affinity for ST2 ligand. To illustrate, ST2 ligand proteins find use as reagents that may be employed by those conducting "quality assurance" studies, e.g., to monitor shelf life and stability of ST2 proteins under different conditions. ST2 ligand may be employed in a binding affinity study to measure the biological activity of an ST2 protein that has been stored at different temperatures, or produced in different cell types. ST2 ligands may be used in determining whether biological activity is retained after modification of an ST2 protein (e.g., chemical modification, truncation, mutation, etc.). The binding affinity of the modified ST2 protein for an ST2 ligand is compared to that of an unmodified ST2 protein to detect any adverse impact of the modifications on biological activity of ST2. The biological activity of an ST2 protein thus can be ascertained before it is used in a research study, for example.

A different use of an ST2 ligand is as a reagent in protein purification procedures. ST2 ligand or ST2 ligand/Fc fusion proteins may be attached to a solid support material by conventional techniques and used to purify ST2 by affinity chromatography.

As illustrated in example 8, ST2 is expressed on certain lymphoma cell lines, including both Hodgkin's lymphoma and Burkitt's lymphoma-derived cell lines. The ST2 ligand of the present invention thus finds further use as a carrier to deliver a diagnostic or therapeutic agent to such cells, or to other cell types that express ST2 on the cell surface. The cells may be contacted with an ST2 ligand having a diagnostic or therapeutic agent attached thereto, in either in vitro or in vivo procedures.

One example of such use involves in vitro assays in which a particular type of $ST2^+$ cancer cells are exposed to a conjugate comprising a therapeutic agent attached to an ST2 ligand, to assess whether the particular agent exhibits a cytotoxic effect on the cancer cells. A number of different therapeutic agents attached to ST2 ligands may be included to compare the relative effectiveness of the agents in treating the particular cancer cells in the assay. ST2 ligands bearing diagnostic agents may be employed to detect the presence of $ST2^+$ cells.

Suitable diagnostic or therapeutic agents include, but are not limited to, radionuclides, drugs, toxins, chromophores, fluorescent compounds, enzymes that catalyze a colorimetric or fluorometric reaction, and the like, with the particular agent being chosen according to the intended application. Examples of drugs include those used in treating various forms of cancer, e.g., mechlorethamine, procarbazine, prednisone, dacarbazine, nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine or vinblastine, and antibiotics such as calicheamycin, bleomycin, doxorubicin, daunorubicin, and derivatives or combinations thereof. Among the toxins that may be employed are ricin, abrin, saporin toxin, diptheria toxin, *Pseudomonas aeruginosa* exotoxin A, ribosomal inactivating proteins, mycotoxins such as trichothecenes, and derivatives, fragments, and single polypeptide chains thereof. Radionuclides suitable for diagnostic use include, but are not limited to, $^{123}I$, $^{131}I$, $^{99m}Tc$, $^{111}In$, and $^{76}Br$. Among the radionuclides suitable for therapeutic use are $^{131}I$, $^{211}At$, $^{77}Br$, $^{186}Re$, $^{212}Pb$, $^{212}Bi$, $^{109}Pd$, $^{64}Cu$, and $^{67}Cu$.

The agents may be attached to the ST2 ligand using any of the conventional methods by which such compounds are attached to polypeptides in general. Functional groups on amino acid side chains of an ST2 ligand may be reacted with functional groups on a desired agent to form covalent bonds, for example. The agent may be covalently linked to ST2 ligand via an amide bond, hindered disulfide bond, acid-cleavable linkage, and the like, which are among the linkages that may be chosen according to such factors as the structure of the desired agent. Alternatively, the ST2 ligand or the agent may be derivatized to generate or attach a desired reactive functional group. The derivatization may involve attachment of one of the bifunctional coupling reagents available for linking various molecules to proteins (Pierce Chemical Company, Rockford Ill.). A number of techniques for radiolabeling proteins are known. Radionuclide metals may be attached to ST2 ligand using a suitable bifunctional chelating agent, examples of which are described in U.S. Pat. Nos. 4,897,255 and 4,965,392.

The present invention provides compositions (including pharmaceutical compositions) comprising an effective amount of a purified ST2 ligand polypeptide and a suitable diluent, excipient, or carrier. Such carriers will be nontoxic to patients at the dosages and concentrations employed. Ordinarily, the preparation of such compositions entails combining a mammalian ST2 ligand poly-peptide or derivative thereof with buffers, antioxidants such as ascorbic acid, low molecular weight (less than about 10 residues) peptides, proteins, amino acids, carbohydrates including glucose, sucrose, or dextrans, chelating agents such as EDTA, glutathione, or other stabilizers and excipients. Neutral buffered saline is one appropriate diluent. In one embodiment of the invention, the pharmaceutical composition comprises ST2 ligand having a diagnostic or therapeutic agent attached thereto, and a suitable diluent, excipient, or carrier.

For diagnostic or therapeutic use, the compositions are administered in a manner and dosage appropriate to the indication and the patient. Administration may be by any suitable route, including but not limited to continuous infusion, local infusion during surgery, sustained release from implants (gels, membranes, and the like), or intravenous injection.

The compositions of the present invention may contain an ST2 ligand protein in any form described herein, including variants, derivatives, and biologically active fragments thereof. In one embodiment of the invention, the composition comprises a soluble human ST2 ligand protein. Such a protein may comprise the extracellular domain of human ST2 ligand fused to an Fc polypeptide, as described above.

Oligomeric Forms of ST2 Ligand

Encompassed by the present invention are ST2 ligand polypeptides in the form of oligomers, such as dimers or trimers. Such oligomers may be naturally occurring or produced by recombinant DNA technology. The present invention provides oligomers of ST2 ligands (preferably the extracellular domain or a fragment thereof), linked by disulfide bonds or expressed as fusion proteins with or without spacer amino acid linking groups. Oligomers may be formed by disulfide bonds between cysteine residues on different ST2 ligand polypeptides, for example.

ST2 ligand oligomers may be prepared using polypeptides derived from immunoglobulins. Preparation of fusion proteins comprising heterologous polypeptides fused to various portions of antibody-derived polypeptides (including the Fc domain) has been described, e.g., by Ashkenazi et al., (*PNAS USA* 88:10535, 1991) and Byrn et al., (*Nature* 344:677, 1990), hereby incorporated by reference. In one embodiment of the invention, an ST2 ligand dimer is created by fusing an ST2 ligand to the Fc region of an antibody (IgG1). The Fc polypeptide preferably is fused to the C-terminus of a soluble ST2 ligand. A gene fusion encoding the ST2 ligand/Fc fusion protein is inserted into an appropriate expression vector. The ST2 ligand/Fc fusion proteins are expressed in host cells transformed with the recombinant expression vector and allowed to assemble much like antibody molecules, whereupon interchain disulfide bonds form between Fc polypeptides to yield divalent ST2 ligand. If fusion proteins are made with both heavy and light chains of an antibody, it is possible to form an ST2 ligand oligomer with as many as four ST2 ligand extracellular regions.

The term "Fc polypeptide" as used herein includes native and mutein forms of polypeptides derived from the Fc region of an antibody. Truncated forms of such polypeptides containing the hinge region that promotes dimerization are also included. One suitable Fc polypeptide, described in PCT application WO 93/10151, is a single chain polypeptide extending from the N-terminal hinge region to the native C-terminus. A mutein of this Fc polypeptide is described in example 1 below. The mutein exhibits reduced affinity for Fc receptors.

Alteratively, one can join ST2 ligand polypeptides via a peptide linker. Peptide linkers suitable for joining polypeptides are known, and may be employed by conventional techniques. Fusion proteins comprising ST2 polypeptides linked by peptide linkers may be produced by recombinant DNA technology. In a preferred embodiment, two soluble ST2 ligand polypeptides are joined by peptide linkers.

Expression Systems

The present invention provides recombinant expression vectors for expression of ST2 ligand, and host cells transformed with the expression vectors. Any suitable expression system may be employed. The vectors include an ST2 ligand DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the ST2 ligand DNA sequence. Thus, a promoter is operably linked to an ST2 ligand DNA sequence if the promoter controls the transcription of the ST2 ligand DNA sequence. An origin of replication, which confers the ability to replicate in the desired host cells, and a selection gene by which transformants are identified, are generally incorporated into the expression vector.

In addition, sequences encoding appropriate signal peptides that are not native to the ST2 ligand gene can be incorporated into expression vectors. For example, a DNA sequence for a signal peptide (secretory leader) may be fused in frame to the 5' end of an ST2 ligand sequence. A signal peptide that is functional in the intended host cells enhances extracellular secretion of the ST2 ligand polypeptide. The signal peptide is cleaved from the ST2 ligand polypeptide upon secretion of ST2 ligand from the cell.

Suitable host cells for expression of ST2 ligand polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce ST2 ligand polypeptides using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella typhimurium,* and various other species within the genera Pseudomonas, Streptormyces, and Staphylococcus. In a prokaryotic host cell, such as *E. coli*, an ST2 ligand polypeptide may include an N-terminal methionine residue to facilitate expression of the recombinant polypeptide in the prokaryotic host cell. The N-terminal Met may be cleaved from the expressed recombinant ST2 ligand polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and an ST2 ligand DNA sequence are inserted into the pBR322 vector.

Promoter sequences commonly used for recombinant prokaryotic host cell expression vectors include β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980; and EP-A-36776) and tac promoter (Maniatis, Molecular Cloning: A Laboratory Manual, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in E. coli strain JMB9 (ATCC 37092)) and pPLc28 (resident in E. coli RR1 (ATCC 53082)).

ST2 ligand alternatively may be expressed in yeast host cells, preferably from the Saccharomyces genus (e.g., S. cerevisiae). Other genera of yeast, such as Pichia or Kluyverormyces, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657. Another altemative is the glucose-repressible ADH2 promoter described by Russell et al. (J. Biol. Chem. 258:2674, 1982) and Beier et al. (Nature 300:724, 1982). Shuttle vectors replicable in both yeast and E. coli may be constructed by inserting DNA sequences from pBR322 for selection and replication in E. coli (Amp$^r$ gene and origin of replication) into the above-described yeast vectors.

The yeast α-factor leader sequence may be employed to direct secretion of the ST2 ligand polypeptide. The α-factor leader sequence is inserted between the promoter sequence and the structural gene sequence. See, e.g., Kurjan et al., Cell 30:933, 1982; Bitter et al., Proc. Natl. Acad. Sci. USA 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μ/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μ/ml adenine and 80 μg/ml uracil. Derepression of the ADH2 promoter occurs when glucose is exhausted from the medium.

Mammalian or insect host cell culture systems could also be employed to express recombinant ST2 ligand polypeptides. Baculovirus systems for production of heterologous proteins in insect cells are reviewed by Luckow and Summers, Bio/Technology 6:47 (1988). Established cell lines of mammalian origin also may be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et at. (EMBO J. 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a vital genome as a fragment which may also contain a vital origin of replication (Fiers et al., Nature 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 3:935, 1986). A useful high expression vector, PMLSV N1/N4, described by Cosman et al. (Nature 312:768, 1984) has been deposited as ATCC 39890. Additional useful mammalian expression vectors are described in EP-A-0367566, and in U.S. patent application Ser. No. 07/701,415, filed May 16, 1991, incorporated by reference herein. Other suitable vectors may be derived from retroviruses.

In place of the native signal sequence, a heterologous signal sequence may be added, such as the signal sequence for interleukin-7 (IL-7) described in U.S. Pat. No. 4,965, 195; the signal sequence for interleukin-2 receptor described in Cosman et al., Nature 312:768 (1984); the interleukin-4 signal peptide described in EP 367,566; the type I interleukin-1 receptor signal peptide described in U.S. Pat. No. 4,968,607; and the type II interleukin-1 receptor signal peptide described in EP 460,846.

ST2 Ligand Protein

The present invention provides purified ST2 ligand protein, which may be produced by recombinant expression systems as described above or purified from naturally occurring cells. The ST2 ligand preferably is purified to substantial homogeneity, as indicated by a single protein band upon analysis by SDS-polyacrylamide gel electrophoresis (SDS-PAGE).

One process for producing the ST2 ligand protein comprises culturing a host cell transformed with an expression vector comprising a DNA sequence that encodes ST2 ligand under conditions such that ST2 ligand is expressed. The ST2 ligand protein is then recovered from culture medium or cell extracts, depending upon the expression system employed. As the skilled artisan will recognize, procedures for purifying the recombinant ST2 ligand will vary according to such factors as the type of host cells employed and whether or not the ST2 ligand is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify ST2 ligand. Some or all of the foregoing purification steps, in various combinations, can be employed to provide a substantially homogeneous recombinant protein.

It is also possible to utilize an affinity column comprising the ligand binding domain of ST2 to affinity-purify expressed ST2 ligand polypeptides. Alternatively, the affinity column may comprise an antibody that binds ST2 ligand. Example 7 describes a procedure for employing the ST2 ligand protein of the present invention as an immunogen to generate monoclonal antibodies.

Recombinant protein produced in bacterial culture is usually isolated by initial disruption of the host cells, centrifugation, extraction from cell pellets if an insoluble polypeptide, or from the supenatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express ST2 ligand as a secreted polypeptide. This simplifies purification. Secreted recombinant polypeptide from a yeast host cell fermentation can be purified by methods analogous to that disclosed by Urdal et al. (*J. Chromatog.* 296:17 1, 1984), which includes two sequential, reversed-phase HPLC steps.

Nucleic Acid Fragments

The present invention further provides fragments of the ST2 ligand nucleotide sequences presented herein. Such fragments desirably comprise at least about 14 nucleotides of the sequence presented in SEQ ID NO:1 or SEQ ID NO:3. DNA and RNA complements of said fragments are provided herein, along with both single-stranded and double-stranded forms of the ST2 ligand DNA.

Among the uses of such ST2 ligand nucleic acid fragments is use as a probe. Such probes may be employed in cross-species hybridization procedures to isolate ST2 ligand DNA from additional mammalian species. As one example, a probe corresponding to the extracellular domain of ST2 ligand may be employed. The probes also find use in detecting the presence of ST2 ligand nucleic acids in in vitro assays and in such procedures as Northern and Southern blots. Cell types expressing ST2 ligand can be identified. Such procedures are well known, and the skilled artisan can choose a probe of suitable length, depending on the particular intended application. The probes may be labeled (e.g., with $^{32}p$) by conventional techniques.

Other useful fragments of the ST2 ligand nucleic acids are antisense or sense oligonucleotides comprising a single-stranded nucleic acid sequence (either RNA or DNA) capable of binding to target ST2 ligand mRNA (sense) or ST2 ligand DNA (antisense) sequences. Antisense or sense oligonucleotides, according to the present invention, comprise a fragment of the coding region of ST2 ligand cDNA. Such a fragment generally comprises at least about 14 nucleotides, preferably from about 14 to about 30 nucleotides. The ability to create an antisense or a sense oligonucleotide based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of ST2 ligand proteins.

Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind. to target nucleotide sequences. Other examples of sense or antisense oligonucleotides include those oligonucleotides which are covalently linked to organic moieties, such as those described in WO 90/10448, and other moieties that increase affinity of the oligonucleofide for a target nucleic acid sequence, such as poly-(L-lysine). Further still, intercalating agents, such as ellipticinc, and alkylating agents or metal complexes may be attached to sense or antisense oligonucleotides to modify binding specificities of the antisense or sense oligonucleotide for the target nucleotide sequence.

Antisense or sense oligonucleofides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retroviral vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT application U.S. 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

The following examples are provided to illustrate particular embodiments, and not to limit the scope of the invention.

EXAMPLE 1

Preparation of Soluble ST2/Fc Fusion Protein

This example describes construction of an expression vector encoding a soluble human ST2/Fc fusion protein. The fusion protein was used in the binding assay and screening procedures described in examples 2 and 3.

Isolation of human ST2 cDNA is described in Tominaga et al. (*Biochimica et Biophysica Acta,* 1171:215, 1992), hereby incorporated by reference. The nucleotide and encoded amino acid sequences are also presented. The open reading frame of 328 amino acids includes an N-terminal signal peptide but no transmembrane or cytoplasmic domains.

DNA encoding this soluble human ST2 protein was isolated and amplified in a polymerase chain reaction (PCR). The PCR was conducted by standard procedures, using oligonucleotides that define the termini of the desired fragment as the primers. PCR procedures are described, for example, in Saiki et al. (*Science* 239:487, 1988) and in *Recombinant DNA Methodology,* Wu et al. eds., Academic Press Inc., San Diego, 1989, pp 189–196. The primers employed in the PCR were based on the ST2 DNA sequence presented in Tominaga et al. (supra), and defined the termini of the desired ST2-encoding DNA fragment. The primers comprised additional DNA that added a Sal I restriction site at the 5' end of the amplified fragment, and a Bgl II site at the 3' end. The reaction products of the PCR were digested with Sal I and Bgl II, and the desired fragment was isolated.

A DNA fragment encoding a mutein of the Fc portion of a human IgG1 antibody was also isolated. The Fc mutein DNA and the polypeptide encoded thereby are described in U.S. patent application Ser. No. 08/097,827, entitled "Novel Cytokine Which is a Ligand for OX40", filed Jul. 23, 1993, which application is hereby incorporated by reference. The mutein DNA was derived from a native Fc polypeptide-encoding DNA by site-directed mutagenesis conducted essentially as described by Deng and Nickoloff (*Anal. Biochem.* 200:81, 1992). The amino acid sequence of the mutein is identical to that of the native Fc polypeptide described in PCT application WO 93/10151, except that amino acid 19 has been changed from Leu to Ala, amino acid 20 has been changed from Leu to Glu, and amino acid 22 has been changed from Gly to Ala. The mutein offers the advantage of reduced affinity for Fc receptors. A DNA fragment encoding this Fc mutein was isolated by digestion with the restriction endonucleases Bgl II (which cleaves near the 5' end of the Fc mutein DNA) and Not I (which cleaves just downstream of the Fc mutein DNA).

The human ST2 DNA and the Fc mutein-encoding DNA were ligated into a SalI/Not I-digested expression vector pDC409. The ST2 DNA was positioned upstream of the Fc DNA in the same reading frame in the resulting recombinant vector. pDC409, a mammalian expression vector that also replicates in *E. coli,* is similar to pDC406 (McMahan et al., *EMBO J.* 10:2821, 1991). The multiple cloning site (mcs) of pDC409 differs from that of pDC406 in that it contains additional restriction sites and three stop codons (one in each reading frame). A T7 polymerase promoter downstream of the mcs facilitates sequencing of DNA inserted into the mcs.

COS-7 cells (ATCC CRL 1651) were transfected with the recombinant expression vector and cultured to allow transient expression of the ST2/Fc fusion protein, which is secreted into the culture medium. The fusion protein was purified using a protein A sepharose column (Pharmacia Biotech, Piscataway, N.J.).

EXAMPLE 2

Screening Cells for ST2/Fc Binding

ST2 proteins exhibit structural similarity to IL-1 receptors, as discussed above. Thus, the human ST2/Fc fusion protein prepared in example 1 was tested for the ability to bind IL-1α and IL-1β (March et al. *Nature (Lond.)* 315:641, 1985), as well as IL-1 receptor antagonist protein (Eisenberg et al. *Nature* 343:341, 1990; Hannum et al., *Nature* 343:336, 1990; and Carter et al., *Nature* 344:633, 1990). IL-1 receptor antagonist (IL-1ra) binds to IL-1 receptors, but does not transduce a signal. IL-1ra competes with IL-1 for binding to endogenous IL-1 receptors, thus inhibiting biological effects mediated by IL-1.

The ST2/Fc fusion protein was indirectly bound to the chip of a biosensor unit, as follows. Goat anti-human IgG directed against the Fc region (Jackson Immunoresearch Laboratories, Inc., West Grove, Pa.) was chemically bound to the chip of a BIAcore Processing Unit (Pharmacia Biosensor) by standard techniques. The ST2/Fc fusion protein was then bound to the immobilized goat anti-human IgG via binding of the IgG to the Fc moiety of the fusion protein. Next, a solution of IL-1α, IL-1β, or IL-1ra was allowed to flow across the chip. No binding of IL-1α, IL-1β, or IL-1ra to the immobilized ST2/Fc protein was detected.

Thus, an effort to identify a protein that binds ST2 was begun. Various cell types were screened for the ability to bind ST2/Fc, to identify candidate cells useful as nucleic acid sources in an attempt to clone an ST2 ligand. Cells were incubated with ST2/Fc, followed by a biotinylated anti-human Fc antibody, followed by streptavidin-phycoerythrin (Becton Dickinson). The biotinylated antibody was purchased from Jackson Immunoresearch Laboratories. Streptavidin binds to the biotin molecule attached to the anti-human Fc antibody, which in turn binds to the Fc portion of the ST2/Fc fusion protein. Phycoerythrin is a fluorescent phycobiliprotein which serves as a detectable label. The level of fluorescence signal was measured for each cell type using a FACScan® flow cytometer (Becton Dickinson).

Of the cells screened, neural cell lines, a folicular dendritic cell line, and a murine T-cell lymphoma line were positive for ST2/Fc binding. A human neural cell line designated A-172 was chosen as a nucleic acid source for an attempt to clone an ST2 ligand protein, as described in example 3.

EXAMPLE 3

Isolation of Human ST2 Ligand cDNA cDNA encoding human ST2 ligand was isolated as follows. The nucleotide sequence of this isolated DNA and the amino acid sequence encoded thereby are presented in SEQ ID NO:1 and SEQ ID NO:2.

A cDNA library was prepared by inserting cDNA derived from the cell line designated A-172 into a mammalian expression vector designated pDC4 10. A-172 is a human glioblastoma cell line described in *J. Natl. Cancer Inst. (Bethesda)* 51:1417–1423, 1973, and available from the American Type Culture Collection under accession no. ATCC CRL 1620. The cDNA was prepared by conventional techniques, using oligo-dT primers. pDC410 is identical to the pDC409 vector (see example 1 ), except that the EBV origin of replication of pDC409 is replaced by DNA encoding the SV40 large T antigen (driven from an SV40 promoter).

*E. coli* strain DH10B cells transfected with the A-172 cDNA library in pDC410 were grown on agar plates by standard techniques. Colonies were scraped from each plate, pooled, and plasmid DNA prepared from each pool. The pooled DNAs, each representing about 2000 colonies, were then used to transfect a sub-confluent layer of CV-1/EBNA-1 cells using DEAE-dextran followed by chloroquine treatment, similar to that described by Luthman et al., *Nucl. Acids Res.* 11:1295, 1983) and McCutchan et al., *J. Natl. Cancer Inst.* 41:351, 1986). The CV-1/EBNA-1 cell line (ATCC CRL 10478) constitutively expresses EBV nuclear antigen-1 driven from the CMV immediate-early enhancer/promoter. CV1-EBNA-1 was derived from the African Green Monkey kidney cell line CV-1 (ATCC CCL 70), as described by McMahan et al. (*EMBO J.* 10:2821, 1991).

In order to transfect the CV-1/EBNA-1 cells with the cDNA library, the cells were maintained in complete medium (Dulbecco's modified Eagle's media (DMEM) containing 10% (v/v) fetal calf serum (FCS), 50 U/ml penicillin, 50 U/ml streptomycin, 2 mM L-glutamine) and were plated at a density of $2 \times 10^5$ cells/well on single-well chambered slides (Lab-Tek). Slides were pretreated with 1 ml human fibronectin (10 ug/ml in PBS) for 30 minutes followed by one wash with PBS. Media was removed from the adherent cell layer and replaced with 3.0 ml complete medium containing 75 µM chloroquine sulfate. 0.2 mls of DNA solution (2 µg DNA, 33 µg/µl DEAE-dextran in complete medium containing chloroquine) were then added to the cells and incubated for 2 hours. Following the incubation, the media was removed and the cells shocked by addition of complete medium containing 10% DMSO for 2.5 to 20 minutes, followed by replacement of the solution with fresh complete medium. The cells were cultured for 2 to 3 days to permit transient expression of the inserted sequences.

Transfected monolayers of CV-1/EBNA-1 cells were assayed for expression of a protein capable of binding the human ST2/Fc fusion protein produced in example 1. The two-step screening process involved incubating cells with non-radiolabeled ST2/Fc followed by $^{125}$I-mouse anti-human Fc antibody. The antibody will bind to the Fc portion of any ST2/Fc fusion protein that has bound to the cells. The mouse anti-human Fc antibody was obtained from Jackson Immunoresearch Laboratories, Inc., West Grove, Pa., and was labeled with $^{125}$I using the standard chloramine-T method.

The screening was conducted by slide autoradiography essentially as described by Gearing et al. (*EMBO J.* 8:3667, 1989). Transfected CV-1/EBNA-1 cells (adhered to chambered slides) were washed once with binding medium with nonfat dry milk (BM-NFDM) (RPMI medium 1640 containing 25 mg/ml bovine serum albumin (BSA), 2 mg/ml sodium azide, 20 mM HEPES, pH 7.2, and 50 mg/ml nonfat dry milk). Cells were then incubated with ST2/Fc in BM-NFDM for 2 hours at room temperature. After incubation, the cell monolayers in the chambered slides were washed twice with BM-NFDM to remove unbound ST2/Fc fusion protein and then incubated with the above-described $^{125}$I-mouse anti-human IgG (a 1:100 dilution) for 2 hours at room temperature.

The cells were washed twice with BM-NFDM, followed by two washes with phosphate-buffered saline (PBS) to remove unbound $^{125}$I-mouse anti-human Fc antibody. Cells then were fixed by incubating for 30 minutes at room temperature in 2.5% glutaraldehyde in PBS, pH 7.3, washed twice in PBS and air dried. The chambered slides containing the cells were exposed on a Phophorimager (Molecular Dynamics) overnight, then dipped in Kodak GTNB-2 photographic emulsion (5×dilution in water) and exposed for 3–5 days at room temperature in a light proof box. The slides were then developed for approximately 4 minutes in Kodak D19 developer (40 g/500 ml water), rinsed in water and fixed in Agfa G433C fixer. The slides were individually examined with a microscope at 25–40×magnification and positive cells expressing an ST2 binding protein were identified by the presence of autoradiographic silver grains against a light background.

Using this slide autoradiography approach, approximately 550,000 cDNA clones were screened in pools of approximately 2,000 clones, and two positive pools were identified. The positive pools were broken down into smaller pools, which were screened for the ability to bind ST2/Fc followed by the $^{125}$I-mouse anti-human IgG. After several rounds of screening pools representing progressively smaller numbers of clones, individual clones positive for ST2/Fc binding were isolated.

The nucleotide and encoded amino acid sequences of the coding region of a human ST2 ligand cDNA are presented in SEQ ID NOS:1 and 2. The protein of SEQ ID NO:2 is a type I transmembrane protein, with an N-terminal signal peptide (amino acids −23 to −1) followed by an extracellular domain (amino acids 1 to 17 1 ), a transmembrane region (amino acids 172 to 192) and a short cytoplasmic domain (amino acids 193 to 204).

*E. coli* DH10B cells transformed with a recombinant vector containing this ST2 ligand cDNA were deposited with the American Type Culture Collection, Rockville, Md., USA (ATCC) on Jun. 10, 1994 and assigned accession number 69645. The deposit was made under the terms of the Budapest Treaty. The recombinant vector comprises the human ST2 ligand cDNA inserted into the unique Sal I site in the multiple cloning site of the cloning vector GEMBL 18. This cloning vector was derived from elements of the pGEM and EMBL vectors. (See Dente et al., *Nucleic Acids Research*, 11:1645, 1983, and the representative examples of pGEM and EMBL vectors available from Promega Biotech, Madison, Wis.) GEMBL18 contains an ampicillin resistance gene.

EXAMPLE 4

Soluble ST2 Ligand/Fc Fusion protein

An expression vector encoding a soluble human ST2 ligand/Fc fusion protein was constructed as follows. Among the advantages of expressing soluble ST2 ligand as such a fusion protein is that the Fc moiety facilitates the protein purification process by binding to Protein A or Protein G on an affinity chromatography matrix.

DNA encoding the signal peptide and extracellular domain of human ST2 ligand (amino acids −23 through 171 of SEQ ID NO:2) was isolated and amplified by polymerase chain reaction (PCR), using the human ST2 ligand cDNA isolated in example 3 as the template. The PCR was conducted by standard procedures, using oligonucleotide primers that define the termini of the desired fragment and add restriction sites useful for inserting the amplified DNA into a vector.

The thus-isolated ST2 ligand DNA and DNA encoding an Fc polypeptide are inserted into a mammalian expression vector such that the Fc-encoding DNA is fused to the 3' end of the ST2 ligand DNA. The Fc polypeptide was the Fc mutein described in example 1. The vector was mammalian expression vector pDC409, also described in example 1. *E. coli* cells were transfected with the ligation mixture, and the desired recombinant vector was isolated from the transformants.

COS-7 cells were transfected with the recombinant vector and cultured to produce the soluble ST2 ligand/Fc fusion protein, which was secreted into the culture medium. This fusion protein also can be expressed in the above-described CV 1/EBNA cells. The ST2 ligand/Fc proteins are believed to form dimers, wherein two such fusion proteins are joined by disulfide bonds that form between the Fc moieties thereof. The protein was recovered from the culture medium by a procedure that included affinity chromatography on a Protein A-bearing chromatography column.

EXAMPLE 5

Northern Blot Analysis

The presence of ST2 ligand mRNA in various cell types was investigated by Northern blot analysis, using standard techniques. The blot was probed with the entire cDNA insert of the human ST2 ligand clone isolated in example 3, washed twice in 0.2×SSC, 0.1% SDS for 30minutes at 55° C., then washed twice in 0.1×SSC, 0.1% SDS for 30 minutes at 63° C.

The predominant message size was about 1.8 kb. A faint higher molecular weight band also was visualized. This ST2 ligand mRNA was detected in the A172 cell line described in example 1; the EBV-positive Burkitt's lymphoma cell line Raji; a rat neural cell line designated B200, which was derived from a glial type tumor; and the murine pre-B lymphocyte cell line designated 70Z/3. The 70Z/3 cells were chosen as a nucleic acid source for cloning a murine ST2 ligand, as described in example 6.

EXAMPLE 6

Isolation of Murine ST2 Ligand cDNA cDNA encoding murine ST2 ligand was isolated by cross-species hybridization, as follows. The nucleotide sequence of this isolated DNA and the amino acid sequence encoded thereby are presented in SEQ ID NO:3 and SEQ ID NO:4.

A cDNA library was prepared by inserting cDNA derived from the murine cell line designated 70Z/3 into the phage vector λgt10. 70Z/3 is a murine pre-B lymphocyte cell line (Paige et al., *J. Immunol.* 121:641, 1978) available from the American Type Culture Collection under accession no. ATCC TIB 158.

The cDNA library was screened with a probe derived from the human ST2 ligand clone isolated in example 3. The probe was prepared by a variation of PCR, employing only one primer and including $^{32}$P-dCTP in the reaction mixture. The primer was an oligonucleotide complementary to the 3' end of the ST2 ligand coding region. The reaction products comprised single-stranded DNA labeled via incorporation of the $^{32}$P-dCTP. Single-stranded labeled DNA corresponding to the entire coding region and a small portion of the 5' non-coding region of the human ST2 ligand DNA was thus prepared and employed as a probe.

A murine clone that hybridized to the probe was isolated, and the nucleotide sequence of the cDNA insert of the recombinant phage was determined. The nucleotide sequence of this isolated DNA and the amino acid sequence encoded thereby are presented in SEQ ID NO:3 and SEQ ID NO:4. This murine ST2 ligand DNA is 82% identical to the human ST2 ligand DNA of SEQ ID NO: 1 (87% identical in the coding regions).

The murine cDNA lacked an initiation codon, and thus was believed to lack N-terminal amino acid residues within the signal peptide. The protein of SEQ ID NO:4 comprises a partial signal peptide (amino acids −21 to −1 of SEQ ID NO: 4), an extracellular domain (amino acids 1 to 170), a transmembrane region (amino acids 171 to 191 ), and a short cytoplasmic domain (amino acids 192 to 203).

DNA that encoded a complete signal peptide (containing an initiator methionine) at the N-terminus of a soluble murine ST2 ligand was isolated by polymerase chain reaction (PCR), as follows. The 5' primer employed in the PCR was an oligonucleotide that included the codons for amino acids −22 and −21 of the human sequence of SEQ ID NO:1 (Met-Ala), followed by the codons for the first three amino acids of the murine sequence of SEQ ID NO:3 (Ala-Gly-Ala). The 3' primer defined the 3' end of the sequence encoding the extracellular domain. The amplified DNA thus encoded a soluble ST2 ligand comprising Met-Ala followed by residues −21 to 170 of the murine ST2 ligand amino acid sequence of SEQ ID NO:4.

DNA encoding a full length murine ST2 ligand may be isolated by employing a 3' primer that defines the 3' end of the coding region, in place of the 3' primer defining the 3' end of the extracellular domain. In an alternative procedure, a DNA fragment comprising the 5' end of the soluble murine ST2 ligand-encoding DNA amplified above (including the codons for Met-Ala) was isolated. The fragment was produced by digestion with a restriction enzyme that cleaves within a site added by the 5' primer, and with Hind III, which cleaves at a site in the extracellular domain. This fragment is joined to a second DNA comprising the 3' end of the murine ST2 ligand coding region by ligation at the Hind III site. The DNAs isolated as described above are inserted into an appropriate expression vector.

EXAMPLE 7

Monoclonal Antibodies to ST2 Ligand

This example illustrates the preparation of monoclonal antibodies to ST2 ligand. ST2 ligand is expressed in mammalian host cells such as COS-7 or CV-1/EBNA-1 cells and purified using ST2/Fc affinity chromatography. Purified ST2 ligand (or a fragment thereof such as the extracellular domain) can be used to generate monoclonal antibodies against ST2 ligand using conventional techniques, such as those described in U.S. Pat. No. 4,411,993.

Briefly, mice are immunized with ST2 ligand emulsified in complete Freund's adjuvant and injected subcutaneously or intraperitoneally in amounts ranging from 10–100 μ. Ten to twelve days later, the immunized animals are boosted with additional ST2 ligand emulsified in incomplete Freund's adjuvant. Mice are boosted thereafter on a weekly to bi-weekly immunization schedule. Serum samples are periodically taken by retro-orbital bleeding or tail-tip excision for testing by dot blot assay or ELISA (Enzyme-Linked Immunosorbent Assay), for ST2 ligand antibodies.

Following detection of an appropriate antibody titer, positive animals are provided one last intravenous injection of ST2 ligand in saline. Three to four days later, the animals are sacrificed, and spleen cells are harvested and fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified ST2 ligand by adaptations of the techniques disclosed in Engvall et al. (*Immunochem.* 8:871, 1971) and in U.S. Pat. No. 4,703,004. A preferred screening technique is the antibody capture technique described in Beckmann et al. (*J. Immunol.* 144:4212, 1990). Positive hybridoma cells can be injected intraperitoneally into syngeneic BALB/c mice to produce ascites containing high concentrations of anti-ST2 ligand monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to ST2 ligand.

EXAMPLE 8

Cells Expressing ST2

Cells expressing ST2 on the cell surface were detected by their ability to bind an antibody directed against ST2. The antibody was a monoclonal antibody generated by conventional techniques using a human ST2/Fc fusion protein as the immunogen.

Among the cells that bound the antibody were KM-H2 cells, a Hodgkin's lymphoma cell line (Kamesaki et al., *Blood* 68:285, 1986), kindly provided by Hans G. Drexler, DSM, Braunschweig, Germany. KM-H2 is an EBV⁻ tumor cell line derived from a malignant pleural effusion of a human patient with stage IV mixed cellularity Hodgkin's Disease. Two Burkitt's lymphoma cell lines, designated Namalwa and DG-75, also bound the antibody. The Namalwa cell line (American Type Culture Collection accession no. ATCC CRL 1432) is described in *Int. J. Cancer* 10:44, 1972. DG-75, available from the German Collection of Microorganisms and Cell Cultures (DSM), Braunschweig, Germany, under accession no. ACC 83, is described in Ben-Bassat et al., *Int. J. Cancer* 19:27, 1977.

What is claimed is:

1. An isolated DNA sequence encoding an ST2 ligand polypeptide, wherein said ST2 ligand comprises an amino acid sequence selected from the group consisting of amino acids −23 to 204 of SEQ ID NO:2, amino acids 1 to 204 of SEQ ID NO:2, and amino acids 1 to 203 of SEQ ID NO:4.

2. An isolated DNA sequence according to claim 1, wherein said DNA sequence comprises a nucleotide sequence selected from the group consisting of nucleotides 88 to 771 of SEQ ID NO:1, nucleotides 157 to 771 of SEQ ID NO:1, and nucleotides 64 to 675 of SEQ ID NO:3.

3. An expression vector comprising a DNA sequence according to claim 1.

4. A process for preparing an ST2 ligand polypeptide, comprising culturing a host cell transformed with a vector according to claim 3 under conditions promoting expression of ST2 ligand, and recovering the ST2 ligand polypeptide.

5. An isolated DNA sequence encoding a soluble human ST2 ligand protein, wherein said ST2 ligand comprises an amino acid sequence selected from the group consisting of amino acids −23 to 171 of SEQ ID NO:2 and 1–171 of SEQ ID NO:2.

6. An isolated DNA sequence according to claim 5, wherein said DNA sequence comprises a nucleotide sequence selected from the group consisting of nucleotides 88 to 669 of SEQ ID NO:1 and nucleotides 157 to 669 of SEQ ID NO:1.

7. An expression vector comprising a DNA sequence according to claim 3.

8. A process for preparing an ST2 ligand polypeptide, comprising culturing a host cell transformed with a vector according to claim 7 under conditions promoting expression of ST2 ligand and recovering the ST2 ligand polypeptide from the culture.

9. An isolated DNA which hybridizes to a nucleotide sequence selected from the group consisting of nucleotides 88 to 771 of SEQ IQ NO:1 and nucleotides 64 to 675 of SEQ ID NO:3 under highly stringent conditions, wherein said isolated DNA encodes a native mammalian ST2 ligand polypeptide that binds ST2.

10. An expression vector comprising a DNA sequence according to claim 9.

11. A process for preparing an ST2 ligand polypeptide, comprising culturing a host cell transformed with a vector according to claim 8 under conditions promoting expression of ST2 ligand, and recovering the ST2 ligand polypeptide.

12. A purified ST2 ligand polypeptide, wherein said ST2 ligand is encoded by a DNA according to claim 5.

13. A conjugate comprising a diagnostic or therapeutic agent attached to an ST2 ligand protein according to claim 12, wherein said agent is a radionuclide chromophore, fluorescent compound or enzyme.

14. A purified soluble ST2 ligand polypeptide which binds ST2 consisting essentially of the extracellular domain of a native mammalian ST2 ligand polypeptide according to claim 12.

15. A conjugate comprising a diagnostic or therapeutic agent attached to a soluble ST2 ligand protein according to claim 14, wherein said agent is a radionuclide chromophore, fluorescent compound or enzyme.

16. A fusion protein comprising a soluble ST2 ligand polypeptide according to claim 14, fused to the N-terminus of an Fc polypeptide.

17. A dimer comprising two fusion proteins according to claim 16, wherein said proteins are joined by disulfide bonds between the Fc polypeptides.

18. A conjugate comprising a diagnostic or therapeutic agent attached to a dimer according to claim 17, wherein said agent is a radionuclide chromophore, fluorescent compound or enzyme.

19. A purified mature human ST2 ligand polypeptide that binds ST2, wherein said ST2 ligand comprises an amino acid sequence selected from the group consisting of residues 1 to 171 of SEQ ID NO:2 and residues 1 to 204 of SEQ ID NO:2, with the proviso that from one to five terminal residues have been deleted from said amino acid sequence.

20. A purified ST2 ligand that comprises the amino acid sequence of residues 1–204 of SEQ ID NO:2.

21. A purified mouse ST2 ligand polypeptide that comprises an amino acid sequence selected from the group consisting of residues 1–203 of SEQ ID NO:4 and residues 1–170 of SEQ ID NO:4.

22. A purified soluble human ST2 ligand comprising the amino acid sequence of residues 1–171 of SEQ ID NO:2.

* * * * *